United States Patent [19]
Katzen

[11] 3,962,416
[45] June 8, 1976

[54] PRESERVED NUTRIENTS AND PRODUCTS

[76] Inventor: Sol Katzen, Hanassi St., No. 62, Herzliya Fituach, Israel

[22] Filed: July 2, 1973

[21] Appl. No.: 375,435

Related U.S. Application Data

[62] Division of Ser. No. 109,566, Jan. 25, 1971.

[52] U.S. Cl. ............................. 424/19; 426/73; 426/74; 426/96; 426/103; 426/656; 424/35; 424/36; 424/344
[51] Int. Cl.² ...................................... A23L 1/30
[58] Field of Search ............... 426/89, 102, 96, 103, 426/656, 205, 213, 218, 73, 293, 289, 302, 74, 141, 208, 276, 305; 424/34, 35, 36, 37, 19, 344; 252/316

[56] References Cited
UNITED STATES PATENTS

| | | | |
|---|---|---|---|
| 1,924,826 | 8/1933 | Anderson | 426/141 |
| 3,434,843 | 3/1969 | Durst | 426/98 |
| 3,495,988 | 2/1970 | Balassa | 426/321 |

*Primary Examiner*—Raymond N. Jones
*Assistant Examiner*—R. Yoncoskie
*Attorney, Agent, or Firm*—Christen & Sabol

[57] ABSTRACT

An encapsulating agent and a nutrient are admixed, and then the encapsulating agent is gelatinized or polymerized under high temperature and pressure so as to encapsulate the nutrient. The encapsulation allows the nutrient to be kept in a dry stabilized state for a long period of time without the loss of potency. Further the encapsulation allows the nutrients to be released into the digestive tract after a predetermined amount of time. The digestive tract solubilizes or digests the encapsulating agent thereby freeing the nutrient. Encapsulation is preferably conducted using a heated extruder or expander. The encapsulating agent may be a high protein vegetable composition, such as, wheat flour gluten, a grain flour or carbohydrate flour. The nutrients may be in particulate or liquid form and can be such things as vitamins, amino acids, lipids, enzymes, inorganic salts (minerals). Additives such as surfactants, can be incorporated into the admixture before the extruding step.

7 Claims, No Drawings

PRESERVED NUTRIENTS AND PRODUCTS

This is a division of application Ser. No. 109,566, filed Jan. 25, 1971.

BROAD DESCRIPTION OF THE INVENTION

The primary purpose of the products of this invention is to supply the body with its necessary nutritional needs and those products are such that can be stored without detrimental effects to the nutrients materials therein.

A high protein vegetable encapsulating agent and at least one nutrient are admixed together. The cereals or other vegetable encapsulating agents are gelatinized or polymerized under elevated pressure and at elevated temperatures. The process causes the nutrients to be encapsulated (coated or protected) by the gelatinized or polymerized encapsulating agent. When cooled and the pressure removed, the resultant product is dry and can be stored for extended periods of time. Storage can easily be before 4 months, or more with nearly complete retention of nutrient potency. The encapsulation prevents the nutrients from being oxidized, reduced, solubilized, sublimated or otherwise diminished in potency which would occur if left in an unprotected state. The product can be sized, if desired or necessary by any convenient means such as grinding. The rate of release of the encapsulated nutrients can be varied according to the solubility of the gelatinized or polymerized encapsulating agent. The time in the digestive tract may vary from about 1 hour to about 8 hours, with 4 hour being normal. Digestion depends upon enzyme action as well as acid hydrolysis. Digestion begins in the mouth by action of salivary amylase (ptyalin) with an optimum pH of 5.5 to 6.5. The stomach pH is 0.85 to 1.00. There are no carbohydrate enzymes in the stomach, but the small intestine contains many enzymes in addition to pancreatic amylase.

The high protein vegetable agent can only contain up to 40 percent by weight of non-protein material such as starch or non-protein nitrogenous material (for example, ammonium phosphate).

Preferably, 100 parts by weight of the encapsulating agent are admixed with about 40 to 50 parts by weight of the nutrients. The board range of nutrients admixed with 100 parts by weight of the encapsulating agent is from about 1 to about 40 parts by weight. That weight range for nutrients includes such additives as surfactants, preservatives, etc.

The encapsulating agent is normally gelatinized or polymerized at a temperature between about 250° to 450°F., preferably at about 350°F. The temperature utilized must be such that the potency of the nutrients and/or additives is not seriously impaired. The pressure utilized will be above atmspheric and will vary with the type of encapsulating agent, nutrients and additives and the operating temperature, but will generally range from about 200 p.s.i. to about 2500 p.s.i. The preferred operating pressure is about 1000 p.s.i. The time of product formation at those pressures and temperatures will vary from about 3 seconds to about 3 minutes, although the preferred time is about 10 seconds.

The product is preferably formed in an extruder or expander such as those manufactured by Wenger Mixer Mfg Co., of Sabetha, Kans.; Sprout Waldron Co., of Muncy, Penn; the V.D. Anderson Co.; and the Bonner Co. If the encapsulating agent is made viscid for the admixing and encapsulating steps by the addition of water, or like material, the end product is made dry by the flashing off (evaporation) of the entrapped water as steam when the product exits from the extruder or expander. The resulting expanded product has air spaces which makes the product brittle and easily ground. This is the preferred method and product. (The end product can be further dried before or after the encapsulating step, if necessary.)

The resultant product can have any shape and is often an irregular shape due to its method of manufacture. The irregular shape is within the scope of the invention because during polymerization or gelatinization of the carrier the nutrients were completely encapsulated. Complete encapsulation of the nutrients is not based on the use of a carrier as a viscate state when the two are admixed. Thus it is seen that the nutrients may be in a dry particulate form for use in this invention. To assure encapsulation the nutrients should have a particle size of about 20 to 200 mesh. If desired, before encapsulation, several types of nutrients many be coparticulated so that each type of nutrients used is contained in each encapsulated unit.

This invention can be used by both man and animal, with the provisions that the individual nutritional material used for either may be slightly varied. This invention may be used to prepare products which contain one or many more nutrients, which contain one or more additives or which utilize one or more encapsulating agents.

The term "nutrient(s)", within the scope of this invention, encompasses hormones, enzymes, pigments, lipids, plasma proteins, inorganic salts, vitamins, and so forth, that are necessary for a proper diet.

DETAILED DESCRIPTION OF THIS INVENTION

The following paragraphs are listings of various nutrients and certain additives which can be admixed with the encapsulating agent to form the final product of this invention.

Examples of vitamins which can be added are listed below: Vitamin A is 3,7-dimethyl-9-(2,6,6-trimethyl-1-cyclohexen-1-yl)-2,4,6-nonatetraen-1-ol, has a melting point of 64°C., and can be produced by total synthesis. The esters of vitamin A are more stable to oxidation. Vitamin A acetate is $C_{22}H_{32}O_2$ and melts at 57° to 58°C. Vitamin A palmitate is $C_{36}H_{60}O_2$, and can be extracted from fish liver oils. Neovitamin A is 5-cis-Vitamin A and is naturally occuring isomer of vitamin A. Vitamin $B_1$ is also termed aneurin and thiamine, and contains a pyrimidine nucleus joined through a methylene group to a thiazole nucleus. Vitamin $B_1$ hydrochloride is 3-(4-amino-2-methylpyrimidly-5-methyl)-4-methyl-5-$\beta$hydroxyethylthiazolium chloride hydrochloride and is usually prepared synthetically. Vitamin $B_1$ monitrate is crystalline and is practically nonhygroscopic. Vitamin $B_2$ is also termed riboflavin and vitamin G, and is 6,7-dimethyl-9-(D-1-ribityl) isoalloxazine. Vitamin $B_2$ phosphate (sodium salt) is termed cytoflav and flavin mononucleotide, and is $C_{17}H_{20}N_4O_9PNa \cdot 2H_2O$. Vitamin $B_6$ is pyridoxine. Vitamin $B_6$ hydrochloride is also termed pyridoxine hydrochoride and is 5-hydroxy-6-methyl-3,4-pyridine- dimethanol hydrochloride. Vitamin $B_{12}$ is also termed cyanocobalamin and is hygroscopic and is crystalline. Vitamin B is also termed fabic acid and vitamin M, and is $C_{19}H_{19}N_7O_6$. Vitamin $B_x$ is also termed p-aminobenzoic acid and is $NH_2C_6H_4COOH$. Calcium pantothenate, $(C_9H_{16}NO_5)$-

$_2$Ca) and panothenic acid are part of the vitamin B complex. Vitamin C is also termed ascorbic acid and L-xyloascorbic acid, and is $C_6H_8O_6$. Vitamin $D_2$ is also termed calciferol and is $C_{28}H_{44}O$. Vitamin $D_2$ p-nitrobenzoate is $C_{35}H_{47}NO_4$. Vitamin $D_2$ allophante is $C_{30}H_{46}N_2O_3$. Vitamin $D_3$ is 7-dehydrocholesterol activated by U.V. irradiation. Vitamin $D_4$ is 22:23 dihydro-vitamin $D_2$. Vitamin E is also termed α-tocopherol and is 2,5,7,8-tetramethyl-2-(4, '8',12'-trimethyldecyl)-6 -chromanol. Vitamin E acetate is also termed α-tocopheryl acetate and is $C_{31}H_{52}O_3$. α-tocopherol is 2,5,8-trimethyl-2-(4',8',12'-trimethyldecyl)-6-chromanol. α-tocopherol is 2,7,8-trimethyl-2-(4',8',1-2'-trimethyldecyl)-6-chromanol. Vitamin F is linoleic or linolenic acid or fats containing those acids. Vitamin K is also termed phylloquinone and is 2-methyl-3-phytyl-1,4-napthoquinone. Vitamine $K_1$ oxide is 2-methyl-3-phytyl-1,4-methyl-3(3,7,11,15,19,23-hexamethyl-2,6,10,14,18,22-tetracosahexaenyl)-1,4-naphthaquinone. Vitamin $L_1$ is found in liver filtrate and vitamin $L_2$ in found in yeast filtrate. Vitamin P is also termed citrin. Meso-inositol is a component of the vitamin B complex, is a vitamin is a dietary requirement for higher forms of animal life, and is a hexahydroxycyclohexane. Sodium ascorbate is $C_6H_7O_6Na$. Vitamin $D_2$ 3,5-dinitrobenzoate is $C_{35}H_{46}N_2O_6$. Vitamin $D_2$ phenylurethan is $C_{35}H_{49}NO_2$. Vitamin $D_3$ p-nitrobenzoate is $C_{34}H_{47}NO_4$. Vitamin $D_3$ 3,5-idinitrobenzoate is $C_{34}H_{46}N_2O_6$. Vitamin $D_3$ allophanate is $C_{29}H_{46}N_2O_3$. Vitamin $D_4$ 3,5-dinitrobenzoate is $C_{35}H_{48}N_2O_6$. Vitamin E allophanate is $C_{31}H_{52}N_2O_4$. Vitamin E p-nitrophenylurethane is $C_{36}H_{54}N_2O_5$.

The carotenoids are any of a class of yellow and red pigments found in various plants and the fat of animals. Most of the members of that class may be classed as tetraterpenes. The liver converts carotenoids into vitamin A. Examples of monocyclic and dicyclic unsaturated hydrocarbon tetraterpenes which can be added are: α-carotene, which is $C_{40}H_{56}$; β-carotene; and ν-carotene. Examples of monocyclic and dicyclic unsaturated hydrocarbon oxygenated tetraterpenes which can be added are: xanthophyll and cryptoxanthin. Xanthophyll also termed lutein, is a dark-brown crystalline, unsaturated compound, $C_{40}H_{56}O_2$ found in plants and in animal fats, and is a dihydroxy derivate of α-carotene. Cryptoxanthin, $C_{40}H_{56}O$, is a monohydroxy derivate of β-carotene.

Amino acids are necessary to an animal so that the animal can synthesize a specific protein for each specific purpose by picking out the desired amino acids from the blood stream and putting them together in the proper order. Proteins are complex compounds of high molecular weight that yield α-amino acids, $RCH(NH_2)COOH$.

The animal organism is unable to synthesize essential amino acids from inorganic nitrogen and hence must obtain them in its diet from plants or other animals. Protein is ingested and hydrolyzed, the hydrolysis being catalyzed by the enzyme flavorings, under acid conditions in the stomach, and by trypsin and other enzymes under approximately neutral to slightly alkaline conditions in the intestines. By successive stages of hydrolysis amino acids are formed and pass through the walls of the intestine into the blood stream, which transports them to other portions of the body. There under the influence of the body's own specific enzymes, they are resynthesized into the tissues characteristic of the organism.

The organism also is able to convert some amino acids into others. Amino acids that can be so formed need not be ingested. On the other hand it is known that certain amino acids cannot be produced by animals, hence they have been termed indispensable or essential amino acids. The term "indispensable" should not be taken to mean that these amino acids are more important than the "dispensable" amino acids, since all natural amino acids undoubtedly are necessary for the development and maintenance of the organism. Indispensable merely means that these amino acids must be supplied in the proteins of the diet, and cannot be synthesized from other amino acids.

Amino acids not only are incorporated into body proteins, but may be degraded to carbon dioxide, water, and ammonia with the liberation of about 4 kcal. of energy per gram of protein. The ammonia is eliminated chiefly as urea. Amino acids may serve also as precursors of other biologically important compounds or as agents for the elimination of other substances.

The α-amino acids include neutral α-amino acids, i.e., those having an equal number of amino groups and carboxyl groups, basic α-amino acids, i.e., those having more basic groups than carboxyl groups, and acidic α-amino acids, i.e, those having more carboxyl groups than amino groups. Natural and/or synthetic α-amino acids can be added.

Examples of indispensible or essential α-amino acids or derivatives thereof are 1-arganine, which is 1-amino-4-guanidovaleric acid; 1-arginine hydrochloride, which is $C_6H_{14}N_4O_2·C_6H_3N_3O_7·2H_2O$; 1-histidine, which is α-amino-4-imidazolepropionic acid; dl-histidine; l-histidine dihydrochloride; l-isoleucine, which is α-amino-β-methylvaleric acid; dl-isoleucine; l-alloisoleucine; l-leucine, which is α-aminoisocaproic acid; dl-leucine; l-lysine, which is αε-diaminocaproic acid; l-lysine monopicrate, which is $C_6H_{14}N_2O_2·C_6H_3N_3O_7$; l-lysine dihydrochloride, which is $C_6H_{14}N_2O_2·2HCl$; l-lysine monohydrochloride, which is $C_6H_{14}N_2O_2·HCl$; dl-lysine dihydrochloride; dl-lysine monohydrochloride; dl-lysine monopicrate; l-methionine, which is γ-amino-α-methylmercaptobutyric acid; dl-methionine; l-phenylanine, which is $C_6H_5CH(NH_2)CO_2H$; d-phenylalanine; dl-phenylalanine; l-phenylalanine picrolonate, which is $C_6H_5CH_2(NH_2)CO_2H$; d-phenylalanine, dl-phenylalanine: l-phenylalanine picrolonate, which is $C_9H_{11}NO_2·C_{10}H_8N_4O_5$; dl-phenylalanine picrate, which is $(C_9H_{11}NO_2·C_6H_3N_3O_7$; l-threonine, which is α-amino-β-hydroxybutyric acid; the monobenzoyl derivative of l-threonine, which is $C_{11}H_{13}NO_4$; l-threonine picrate, which is $C_{10}H_{12}N_4O_{10}$; dl-threonine: hemihydrate; dl-theonine; L-tryptophan, which is 1-α-amino-3-indolepropionic acid; l-trytophan hydrochloride, which is $C_{11}H_{12}N_2O_2·HCl$; l-tryptophan picrate, which is $C_{11}H_{12}N_2O_2·C_6H_6N_3O_7$; dl-tryptophan l-valine, which is α-aminoisovaleric acid; and dl-valine.

Other α-amino acids and derivatives thereof which can be added, for example, are the following neutral α-amino acids and derivatives thereof: glycine, which is aminoacetic acid, $CH_2(NH_2)COOH$; tyrosine, which is α-amino-β-(4-bydroxyphenyl) propionic acid; serine, which is α-amino-β-hydroxypropionic acid, $HOCH_2CH(NH_2)COOH$; proline, which is 2-pyrrolinecarboxylic acid; thyroxine, which is α-amino-β-[3,5-diiodo-4-(3,5-diiodo-4-dydroxyphenoxy phenyl] propionic acid; iodogorgoic acid, which is 3,5-diiodotyrosine; cysteine, which is α-amino-β-mercaptopropionic acid, $HSCH_2CH(NH_2)COOH$; cysteine, which is bis-(2-amino-2-carboxyethyl)disulfide; glycine hydrochloride; cysteine hydrochloride and cystine hydrochloride.

Other α-amino acids and derivatives thereof which can be added, for example, are the following acidic α-amino acids: and derivatives thereof: aspartic acid, which is aminisuccinic acid, HOOCCH$_1$CH(NH$_2$.)COOH; and glutamic acid, which is α-aminoglutoric acid, HOOCCH$_2$CH$_2$CH(NH$_2$)COOH; and glutamic acid hydrochloride.

Enzymes are any of a class of complex, naturally occurring, organic substances of unknown compositions that accelerate (catalyze) specific transformations of material in plants and animals. Enzymes are elaborated by cells, but their action is independent of life processes and they are not consumed in the course of their action. They are of importance in the digestion and utilization of food, and in cellular processes. Some enzymes are secreted in an inactive form (Zymogen) and require activation or the presence of another substance (coenzyme) to become effective. Enzymes are classified according to the nature of the substance or reaction they affect.

Examples of enzymes which can be added are pepsin, which is a proteolytic enzyme; trypsin, which is a proteolytic enzyme; D-amino acid oxidase, which is an enzyme containing a protein and a flavin coenzyme (isoalloxazine adenine dinucleotide); L-amino acid oxidase; diatases; zymases; maltases; carbohydrases; carboxylases; nucleases; lypases; oxidases; peptidases; proteases reductases; hydrolases; enolases; esterases; catalases; peroxidases; ureases; and dehydrogenases.

A hormone is a substance, especially a specific organic product of the cells of one part, transported in the body fluid of an organism and producing a specific effect on the activity of cells remote from its source. The term hormone as used herein includes chalones.

Several examples of hormones which can be added are listed below. Adrenalin or epinephrine is a hormone and is 3,4-dihydroxy-α-(methylaminomethyl) benzyl alcohol. Testosterone is a hormone and is Δ$^4$-androsten-17(α)-ol-3-one. Estradiol is a hormone and is 1,3,5-estratriene-3,17α-diol. Diethylstilbestrol is a hormone and is α, α$^1$-diethylstilbenediol. Progesterone is a hormone and is Δ$^4$-pregnene-3,20-dione. Estrone is a hormone and is 1,3,5-estratrien-3-ol-17-one. Estriol is a hormone and is 1,3,5-estratriene-3,16,17-triol. Relaxin is a hormone and it is most likely a polypeptide having a molecular weight of 9,000 to 12,000. Estrone sulfate is a hormone. Androsterone is a hormone and is androstan -3- (α)-ol-17-one. Thyroxine is a hormone and is β-[(3,5-diiodo-4-dydroxyphenoxy)-3,5-diiodophenyl]-alanine. 3,5 3'-Triiodothyronine is a hormone. Stilbestol is diethylstilbestrol, a synthetic compound, which has estrogenic properties. Parathormone is a hormone. Cortisone is a hormone and is 17-hydroxy-11-dehydrocorticosterone. Hydrocortisone is a hormone and is 17-hydroxycorticosterone. Prednisone insulin, protamine insulin and protamine zinc insulin are hormones. Globin insulin is a hormone and is prepared by precipitating insulin with globin. Other hormones are the thyrotrophic hormone, the lactogenic hormone, the adrenocorticotophic hormone, thylakentrin, metakentrin, gastrin, secretin, cholecystokinin, enterogastrone, enterocrinin and erythropocietin.

The lipids are any of a group of substances comprising the fats and other esters, waxes, cerebrosides, phosphatides and related and derived compounds that possess analagous properties. They have been divided into simple, or ternary, lipids, which contain only carbon, hydrogen and oxygen (glycerides, cerides, sterides, etholides), and complex or compound lipids, which contain in addition phosphorous or phosphorous and nitrogen (phospholipides, phosphoamino lipides). The fats can be liquid (oils) or solid. Fats are esters formed by the chemical union of glycerol and fatty acids. Waxes are simple lipids which break down upon hydrolysis to fatty acids and to some alcohol other than glycerol. Examples of lipids which can be added are ethanolamine; the trimethylammonium salts of ethanolamine, the cholines, such as, choline chloride; stearin or glyceryl tristearate; kerasin; lecithins; and cephalins.

A third type of lipid is the derived lipid, such as, the fatty acids. They are water-insoluble and are obtained by the hydrolysis of simple or compounds lipids. Eamples of derived lipids which can be added are linoleic acid, linolenic acid and arachidonic acid.

Some additives can be added. Examples of the additives are surfactants; sweeterers or carbohydrates, such as, sugar; natural and/or artifical falvorings, such as, malt flavorings and artificial vanilla flavoring; citric acid; citric acid monohydrate; non-fatty oils; invert sugar; minerals; perservatives such as BHA and BHT; water; iodized salt; sodium caseinate; sodium iron pyrophosphate; artifical and/or natural colorings; nonfat dry milk; cocoa; lactose; lecithin; niacin; niacinamide; etc. Calcium carbonate can be added to supply calcium. Iron phosphate, ferrous fumarate or ferrous sulfate can be added to supply iron. Magnesium oxide or magnesium sulphate can be added to supply magnesium. Potassium oxide can be added to supply potassium. Dicalcium phosphorous can be added to supply phosphorous and calcium. Potassium iodine can be added to supply iodine. Copper oxide and cupric carbonate can be added to supply copper. Manganese dioxide or maganese sulfate can be added to supply manganese. Zince oxide or zinc sulfate can be added to supply zinc.

Unless otherwise stated all parts and percentages in this specification for the examples are expressed on a weight basis. The following examples illustrate this invention but are not limited to the scope of the invention.

EXAMPLE 1

1 kg. of Vitamin A palmitate, having a rating of 1.7 million I.U. per gram, and was thoroughly admixed with 4 kg. of corn flour. The encapsulating agent was the corn flour and the nutrient was vitamin A palmitate. The admixture was extruded in a extruder manufactured by the Wenger Mixer Mfg. Co. of Sabetha, Kans. The extruder was operated at a pressure of 1000 p.s.i. and has a temperature of 240°F. The temperature used was sufficient to gelatinize the corn flour but yet was not of such a level as to decompose, deactivate or otherwise impair or destroy the potency or effectiveness of the vitamin A palmitate. The gelatinized corn flour completely enclosed individual or groups of particles of vitamin A palmitate. The extruded material was dried, cooled and reduced in size by grinding to particles of a average diameter of about 0.1 min (millimeter). The resultant product contained 340 million I.U. of vitamin A per kg, which is above the conventional market standard of 325,000 I.U. per gram. The resultant product which contained encapsulated dry, stabilized vitamin was stored for two months and was then consumed by a man and a rat. The gelantinized encompassing corn flour was solubilized in the digestive tract, the vitamin A material was released, thereby making the vitamin A activity available to the organism.

EXAMPLE 2

Example 1 was repeated except that an admixture of 3.0 kg. of corn flour and 2.0 kg. of flash desolventized cottonseed flour was used as the encapsulating agent. As the material was extruded, the gelatinized encapsulating agent expanded causing a flash evaporation of steam still trapped therein. When the expanded product was cooled, it contained air spaces. The bulk of the nutrient was encapsulated by the gelatinized corn flour and the polymerized cottonseed flour, even through air spaces were present. The product was easily ground, after being thoroughly dired in a conventional oven, to reduce its particle size to about 0./mim. The dry product was brittle and easily ground. The material was stored for three months and the encapsulated nutrient at that time showed no loss of vitamin A activity during the period.

EXAMPLE 3

1 kg. of a xanthophyll oil containing 100 grams of xanthophyll was admixed with 4 kg. of soybean flour. The admixed material was extruded at a pressure of 1000 p.s.i. and at 230°F. The extruded material was ground until it had an average particle size of 0.1 mm. The resultant product contained 20 grams of encapsulated dry stabilized xanthophyll per kg. of the product. The resultant product was stored for three months without any noticeable loss of the potency of the nutrient.

EXAMPLE 4

Example 1 was repeated except that the admixture also contained 100 grams of an amino acid mixture. The composition of the amino acid admixture was: l-arginine HCl, 8.0 gm; l-histidine $HCl.H_2O$, 4.0gm; dl-isoleucine, 10.8 gm; l-leucine, 15.4 gm; l-lysine HCl, 12.3 gm; dl-methionine, 6.1 gm; dl-phenylalanine, 6.9 gm; dl-threonine, 10.8 gm; dl-tryptophan, 1.8 gm; dl-valine, 13.9 gm; and glycine, 10.0 gm. The resultant product were each fed to chicks without showing the amino acid toxicity that normally accompanies rapid absorption of free amino acids.

EXAMPLE 5

Example 1 was repeated except that the corn flour was replaced with wheat flour. The resultant product was stored for two months without showing any loss of potency of the nutrients.

EXAMPLE 6

Example 2 was repeated except that the corn flour, cottonseed flour mixture was replaced with an equal amount of wheat gluten flour. The resultant product was stored for two months without showing any loss of potency of the nutrients.

EXAMPLE 7

Example 1 was repeated except that the admixture also contained 50 grams of vitamin $B_1$ hydrochloride, 50 grams of vitamin $B_2$, 60 grams of vitamin $B_6$, 50 grams of vitamin $B_{12}$, 20 grams of vitamin $B_r$, 10 grams of vitamin $B_x$, 100 grams of vitamin C, 20 grams of vitamin $D_3$, 10 grams of vitamin $D_4$, 50 grams of vitamin E, 50 grams of vitamin F, 10 grams of phylloquinone and 10 grams of citrin. The resultant product was stored for two months without showing any loss of potency of the nutrients.

EXAMPLE 8

Example 1 was repeated except that 1 kg. of ammonium phosphate was included in the admixture. The resultant product was fed to dairy cows as a source of phosphorus and ammonia without the rapid increase of plama ammonia that usually accompanies the feeding of large amounts of ammonia.

I claim:

1. An encapsulated product which comprises (a) at least one nutrient, which is in particulate form, and (b) a gelatinized carbohydrate or polymerized vegetable high protein encapsulating agent which encapsulates the nutrient particles, said product prepared by: (a) admixing at least one high-protein vegetable encapsulating agent or carbohydrate vegetable encapsulating agent and at least one nutrient, said high protein vegetable encapsulating agent containing only up to 40 percent by weight of starch and non-protein nitrogenous material, from about 1 to about 40 parts by weight of said nutrient being present per 100 parts by weight of said encapsulating agent, said high protein or carbohydrate vegetable encapsulating agent being selected from the group consisting of corn flour, cottonseed flour, soybean flour, wheat flour, and wheat gluten flour and said encapsulating agent being in a viscid state before admixture step (a) because of added water; (b) gelatinizing or polymerizing the encapsulating agent and forming an expanded product therefrom which encompasses the nutrient by extruding the above admixture at a temperature between about 250° to 450° F. and at a pressure between about 200 p.s.i. and about 2500 p.s.i. for a time between about 3 seconds and about 3 minutes, whereby the extrudate expands due to flash evaporation of the water upon exiting from the extruder; and (c) cooling the resultant expanded extrudate to form and encapsulated nutrient product containing air spaces.

2. A product as described in claim 1 wherein the nutrient is a vitamin.

3. A product as described in claim 1 wherein the vitamin is a compound having vitamin A activity.

4. A product as described in claim 1 wherein the encapsulating agent is corn flour.

5. A product as described in claim 1 wherein the encapsulating agent is soybean flour.

6. A product as described in claim 1 wherein said nutrient has a particle size of about 20 to 200 mesh.

7. A product as described in claim 1 wherein only one encapsulating agent is used.

* * * * *